United States Patent [19]

Feve et al.

[11] 4,097,738
[45] Jun. 27, 1978

[54] METHOD OF ANALYSIS OF A SAMPLE OF INSULATING MATERIAL BY PHOTOELECTRONIC SPECTROMETRY

[75] Inventors: Lucette Feve, Gif-sur-Yvette; Rémy Fontaine, Montlhery, both of France

[73] Assignee: Commissariat a l'Energie Atomique, Paris, France

[21] Appl. No.: 751,374

[22] Filed: Dec. 17, 1976

[30] Foreign Application Priority Data

Dec. 19, 1975 France .................................. 75 39096

[51] Int. Cl.² .............................................. H01J 39/00
[52] U.S. Cl. .................................................... 250/305
[58] Field of Search ................... 250/305, 399, 492 R, 250/310, 309

[56] References Cited

U.S. PATENT DOCUMENTS 3,749,926  7/1973  Lee ........................................ 250/305
3,822,383  7/1974  Koike .................................... 250/305

FOREIGN PATENT DOCUMENTS 1,282,498  7/1972  United Kingdom ................. 250/305

*Primary Examiner*—Alfred E. Smith
*Assistant Examiner*—B. Anderson
*Attorney, Agent, or Firm*—Sidney W. Millard

[57] ABSTRACT

The method consists in subjecting a sample of insulating material to photon radiation and in measuring the energy of the photoelectrons emitted by the sample under the action of the radiation. The sample is fixed on a metal sample-holder having a shape such that a portion of this latter is subjected to radiation. The emission of electrons of low energy is thus initiated and the positive charges which appear at the surface of the samples with the emitted electrons are neutralized by creating in the vicinity of the sample surface a space zone in which the electric field is substantially zero.

9 Claims, 2 Drawing Figures

METHOD OF ANALYSIS OF A SAMPLE OF INSULATING MATERIAL BY PHOTOELECTRONIC SPECTROMETRY

This invention relates to a method of analysis of a sample of insulating material by photoelectronic spectrometry and to a sample-holder for carrying out said method.

It is known that photoelectric spectrometry (ESCA method) makes it possible in principle to study the composition of a sample, whether this latter is formed of conducting material or of semiconducting material or of insulating material. This method is based on the energy analysis of photoelectrons emitted by the deep layers of atoms located at the surface of the sample under the action of ultraviolet or X photon radiation of suitable energy. The energy difference between the incident photons and the electrons emitted by the sample to be tested represents the electron binding energy and the composition of the sample can accordingly be deduced therefrom.

However, although this method produces very satisfactory results in the case of conducting or semiconducting samples, special problems arise when the samples are formed of insulating material. In fact, there exists a charge effect produced by ejection of electrons which cannot readily be replaced. This results in the creation of positive charges at the surface of the material. The existence of the charge effect arises from the fact that the vacancies produced by photoemission are not all neutralized by secondary electrons or by the flow of charges within the material. There is accordingly established an equilibrium corresponding to the existence of positive charges at the surface of the sample. The presence of these positive charges at the surface of the sample results in an apparent variation in the binding energies and therefore results in very difficult determination of the structure. The charges slow-down the photoelectrons emitted and this potential produces a displacement of the peaks of photoelectrons towards the low kinetic energies and broadening of these latter as a result of the existence of charge gradients at the surface of the sample.

Up to the present time, it has been endeavored to suppress this charge effect by different methods.

There can first be mentioned the method which consists in depositing a conductive surface film on the insulating sample. This film must be fairly thin (a few angstroms) in order to avoid shielding of the sample. A film of this type is liable to split up into electrically independent islands and removal of the charge is no longer ensured.

It is also possible to mix the previously sputtered sample with a conductive powder (carbn or metal). The disadvantages of this method lie in the destruction of the initial form of the sample and in the danger of a possible parasitic reaction between the conductive powder and the sample under study. Furthermore, it is not established that the insulating grains and the conducting grains are in electrical equilibrium.

A third method consists in making use of an auxiliary electron beam for neutralizing the positive charges. This method calls for the installation of an electron gun in the measuring chamber of the spectrometer. Furthermore, it remains a very difficult matter to regulate the electron flux which is strictly necessary in order to obtain neutralization of the charge.

The precise object of the present invention is to provide a method of photoelectronic spectrometric analysis which overcomes the disadvantages mentioned in the foregoing and effectively ensures suppression of the parasitic charge while making it possible to employ a sample which has not undergone any particular preparation and while also avoiding the use of an auxiliary electron beam.

The method according to the invention for analyzing by photoelectronic spectrometry a sample of insulating material which consists in subjecting said sample to photon radiation and in measuring the energy of the photoelectrons emitted by said sample under the action of said radiation is characterized in that said sample is fixed on a sample-holder, in that said sample-holder which is formed of metal is given a shape such that a portion thereof is subjected to said radiation and the emission of electrons of low energy is thus initiated and that the positive charges which appear at the surface of said samples with said emitted electrons are neutralized by creating in the vicinity of the surface of said sample a space zone in which the electric field is substantially zero.

A space zone in which the field is substantially zero is preferably formed in the vicinity of said sample by fixing this latter at the bottom of a cavity formed within said sample-holder, the shape of said cavity being such that it performs the function of a Faraday cage.

The present invention is also concerned with a sample-holder for carrying out the method.

The sample-holder is characterized in that it is formed of conductive metal, that it is brought to a fixed potential and that provision is made at that end which is directed towards the source of photon radiation for a cavity at the bottom of which is fixed the sample of insulating material, the shape of said cavity being such that at least a portion of its walls is subjected to said radiation and that the bottom of said cavity constitutes a zone in which the electric field is substantially zero.

Said cavity preferably has the shape of a cylinder having a circular cross-section and a chamfered opening.

In accordance with another preferable feature, said cylinder has a depth at least equal to 5 mm along its axis.

A more complete understanding of the invention will in any case be obtained from the following description of one mode of execution of the invention which is given by way of example and not in any limiting sense, reference being made in the description to the following drawings, wherein.

As mentioned earlier, the method according to the invention consists in neutralizing the parasitic positive charges distributed at the surface of the sample by means of photoelectrons emitted by the sample-holder under the action of the incident photons. The sample is placed on a metallic sample-holder and this latter has dimensions which are sufficient to ensure that the sample-holder itself is bombarded with the photon radiation, whereupon this latter in turn emits photoelectrons, some of which have a relatively low kinetic energy and serve to neutralize the surface charge of the insulating sample. However, it is necessary to apply an electric field between the sample-holder and the entrance slit of the spectrometer which serves to measure the energy of the photoelectrons emitted by the sample. Under the action of this field, the photoelectrons of low energy which are emitted by the sample-holder under the action of the electric field cannot have the effect of neutralizing the positive charges located at the surface of the sample. For this reason and in accordance with the method, a substantially zero electric field is produced in the region adjacent to the surface of the sample and of that portion of the sample-holder which emits the photoelectrons under the action of the photon radiation (X-ray or ultraviolet radiation). This does in fact result in neutralization between the positive charges located at the surface of the sample and the electrons of low energy which are emitted by the sample-holder since there is no electric field to prevent displacement of these latter.

Figure 1:
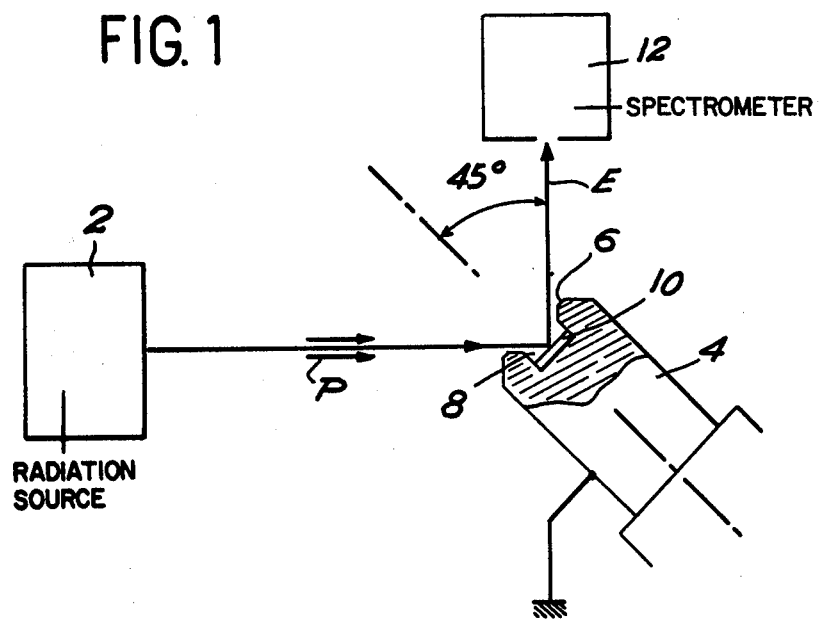
FIG. 1 is a diagrammatic view of the installation as a whole.

FIG. 1 is a diagrammatic illustration of the installation as a whole. This installation comprises an X-ray tube (on the assumption of course that the incident radiation consists of X-radiation) which emits a beam of photons as represented schematically by the arrows P. It would be equally feasible to employ a source of ultraviolet radiation. The installation further comprises a sample-holder 4 as shown diagrammatically in vertical cross-section. As will readily be apparent, the dimensions of the sample-holder have been appreciably increased for the sake of enhanced clarity of the figure. The axis of the sample-holder is located substantially at 45° with respect to the horizontal and the photon beam is also horizontal. At that end which is directed towards the X-ray tube and is designated by the reference 6, the sample-holder is provided with a cavity 8, the sample 10 to be analyzed being placed at the bottom of said cavity. The sample-holder 4 is formed of a metal or more generally of a conducting material and connected to ground. The cavity 8 will be described in greater detail hereinafter. As explained in the foregoing, the sample 10 emits photoelectrons under the action of the photons, the photoelectron beam being indicated in the figure by the arrow E. It is readily apparent that the installation further comprises a spectrometer 12 for measuring the energy of the beam. Said electron beam is formed substantially at right angles to the photon beam.

The conditions to be satisfied by the cavity 8 in order that this latter should effectively perform its double function will now be described in greater detail. As explained earlier, the definition of the shape of said cavity must result from a compromise between two requirements which are a priori contradictory. On the one hand, the cavity 8 must have a sufficiently wide opening to permit ready admission of the exciting photons and emergence of the emitted photoelectrons. Furthermore, it is necessary to form in the vicinity of the surface 14 of the sample 10 a zone in which the electric field is substantially zero.

In order to satisfy the second requirement, the cavity 8 must play the part of a Faraday cage. In order to perform this function in an effective manner, the ideal solution would be to ensure that the cylinder is of substantial depth with respect to the diameter of its opening. On the other hand, such an arrangement would result in considerable reduction in the possibilities of access of the photons to the sample 10.

Figure 2:
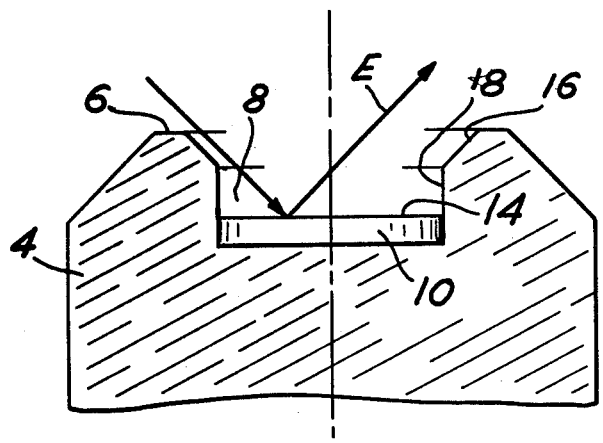
FIG. 2 is a sectional view in elevation showing the end of a sample-holder in accordance with the invention.

For this reason, one possible form of construction of the cavity shown in FIG. 2 is a cylinder having a depth of the order of 5 mm and a diameter of the order of 8 mm. In addition, the edge of the cavity which is directed towards the extremity 6 of the sample-holder 4 is chamfered and therefore constitutes a portion of a frusto-conical surface 16. Since the sample-holder is connected to ground, the really cylindrical portion of the cavity 8 performs the function of a Faraday cage, thus forming in the vicinity of the sample surface 14 a region in which the electric field is substantially zero (bottom of the cavity 8). Moreover, the chamfer 16 provides wide access for the exciting photons.

As has been explained in the foregoing, the photons of the beam P reach on the one hand the sample 10, thus causing the emission of the photoelectrons employed in the measurement and on the other hand the side wall 18 of the cavity, thus causing the formation of photoelectrons having low kinetic energy. As in the bottom of the cavity 8, the electric field is substantially zero; these electrons neutralize the positive charges which are distributed at the surface 14 of the sample 10. This accordingly results in suppression of the positive space charge.

It can readily be understood that forms of cavity other than a flared-out cylinder could be employed. It is only necessary to ensure that these cavities perform the function of a Faraday cage in the portion of greatest depth and therefore in the vicinity of the sample 10 and that they have a sufficient diameter of opening to permit the passage of the photon beam. For example, it would be possible to employ a cavity having the shape of a portion of sphere.

Insofar as it is possible to do so, it is preferable to ensure that the sample-holder emits the maximum number of electrons in order to ensure very rapid neutralization of the charge acquired by the sample; for this reason, it is advantageous to coat the sample-holder with a metal having good electron emissivity such as gold or palladium.

A few examples of analysis of silica and chromium oxide would be given hereinafter, first of all with reference to methods of the prior art and then with reference to the method and device in accordance with the invention.

EXAMPLE 1: Silica $SiO_2$

A measurement is taken of the mean binding energy of the doublet $$2p\ 3/2 \text{ and } 2p\ 1/2$$

of combined silicon in the state of silica.

1. A measurement is first taken by means of a silica layer developed at the surface of a silicon substrate. At the time of measurement by photoelectronic spectrometry, the positive charge effect does not exist by reason of the small thickness of oxide and the electrical conductivity of the substrate. There is found a binding energy $E_1 = 103.6$ eV $\pm\ 0.4$ eV.

2. In a second measurement, a mixture of powdered silica and graphite is prepared in the form of powder in respect of different values of the ratio R : R = mass of silica/mass of carbon ($E_1$ represents the binding energy).

| | |
|---|---|
| R = 1/2 | $E_1 = 106.0$ eV $\pm\ 0.4$ eV |
| R = 1 | $E_1 = 105.4$ eV $\pm\ 0.4$ eV |
| R = 2 | $E_1 = 105.3$ eV $\pm\ 0.4$ eV |
| R = 5 | $E_1 = 104.5$ eV $\pm\ 0.4$ eV |

It is found that, by means of this method the charge effect is not suppressed irrespective of the composition of the mixture.

3. Analysis of SiO₂ on a sample-holder of conventional type.

The measured binding energy is in this case equal to 105.9 eV ± 0.4 eV; an appreciable charge effect is accordingly found to be present.

4. Analysis of a sample of SiO₂ placed within a cavity of a sample-holder of the type which is illustrated in FIG. 2.

The measurements give a binding energy of 103.5 eV ± 0.4 eV. The charge effect is therefore completely suppressed. If the same operation is performed with powdered silica fixed on an adhesive tape placed within the cavity of the same sample-holder, there is found to exist a binding energy of 103.3 eV ± 0.4 eV. It is therefore found that the charge effect is also completely suppressed.

EXAMPLE 2: chromium oxide Cr₂O₃

There is studied the binding energy of the level 2 $p$ 3/2 of chromium in oxide having the formula Cr₂O₃.

1. When a measurement is performed in a conventional manner, starting from oxide formed in a thin film at the surface of the conductive chromium, there is found a binding energy of 575.9 ± 0.4 eV. In other words, there is no charge effect for the reason mentioned earlier in connection with silicon.

2. Analysis of powdered chromium oxide on a conventional sample-holder.

By performing the measurement, the binding energy is found to be 582.4 eV ± 0.4 eV. It is therefore found that a substantial charge effect accordingly exists.

3. Measurement on the basis of a mixture of powdered carbon on an equal weight of powdered chromium oxide.

There is found a binding energy of 577.4 eV ± 0.4 eV. It is therefore found that the charge effect is not completely eliminated.

4. Analysis of powdered chromium oxide on an adhesive tape placed within a cavity in accordance with the invention.

The measurements taken indicate a binding energy of 576.2 eV ± 0.4 eV.

In conclusion, the correct binding energy is always obtained by means of the method and device in accordance with the invention. When adopting the methods of the prior art, the binding energy is more or less erroneous except in the case in which a metal oxide layer of the metal can readily be developed on a substrate of the same metal.

It is therefore found that this modification of said sample-holder which does not give rise to any appreciable modification in the cost of the installation as a whole permits a very appreciable improvement in the determination of the binding energy without thereby entailing the need to subject the sample to be analyzed to any special preparation.

What is claimed is:

1. A method of analysis of a sample of insulative material by photoelectronic spectrometry comprising the steps of:

fixing said sample of insulative material upon a conductive sample-holder;

subjecting a surface of said sample to photon radiation to effect the emission of photoelectrons therefrom, thereby developing positive charges at said surface in consequence of the vacancies resulting from said emission of photoelectrons which are not neutralized by the flow of charges within said sample;

simultaneously subjecting a portion of said conductive sample-holder to said photon radiation to effect the emission therefrom of electrons in the vicinity of said surface of the sample so as to neutralize said positive charges and thereby create a zone adjacent said surface exhibiting a substantially zero electric field; and measuring the energy of photoelectrons emitted by said sample, said energy being compared with the energy of incident photon radiation to determine the electron binding energy of said sample.

2. A method according to claim 1, wherein a said zone in which the field is substantially zero is formed in the vicinity of the sample by fixing said sample at the bottom of a cavity formed in said sample-holder, the shape of said cavity being such that it performs the function of a Faraday cage.

3. A sample holder for retaining a sample of insulating material for analysis by photoelectronic spectrometry wherein said sample is retained in a position for the impingement thereupon of photon radiation, comprising:

a support configured having conductive surfaces defining a cavity for retaining said sample;

said surface being configured for retaining said sample at a bottom portion of said cavity in an orientation for the impingement of said photon radiation upon a surface of said sample to effect the emission of photoelectrons therefrom for analysis and, thereby, developing positive charges at said sample surface in consequence of the vacancies resulting from said emission, said conductive surfaces extending from said bottom portion of said cavity such that at least a portion of said conductive surfaces is exposed to said radiation, said exposed conductive surfaces having an extent wherein, when said portion thereof is exposed to said radiation, electrons are emitted therefrom in the vicinity of said sample surface, so as to neutralize said positive charges and constitute said bottom portion a zone in which the electric field is substantially zero when said sample and conductive surfaces are subjected to said radiation, whereby the energy of said photoelectrons emitted from said sample may be measured and compared with the energy of said photon radiation incident upon said sample to determine the electron binding energy of said sample.

4. A sample-holder according to claim 2, wherein said cavity has the shape of a cylinder having a circular cross-section and a chamfered opening.

5. A sample-holder according to claim 4, wherein said cylinder has a depth at least equal to 5 mm along the axis thereof.

6. A sample-holder according to claim 3 wherein the internal walls of the cavity are coated with a metal having good electron emissivity.

7. A sample-holder according to claim 3 wherein said metal is selected from the group consisting of gold and palladium.

8. A sample-holder according to claim 4 wherein the internal walls of the cavity are coated with a metal having good electron emissivity.

9. A sample-holder according to claim 5 wherein the internal walls of the cavity are coated with a metal having good electron emissivity.

* * * * *